(12) United States Patent
Walsh et al.

(10) Patent No.: US 8,114,051 B2
(45) Date of Patent: Feb. 14, 2012

(54) RETRACTABLE SYRINGE

(75) Inventors: Allan Walsh, Medowie (AU); Feiyan Tan, Foshan (CN)

(73) Assignee: Morgan Meditech Inc.

( * ) Notice: Subject to any disclaimer, the term of this patent is extended or adjusted under 35 U.S.C. 154(b) by 132 days.

(21) Appl. No.: 12/300,617

(22) PCT Filed: Jun. 4, 2007

(86) PCT No.: PCT/AU2007/000779
§ 371 (c)(1),
(2), (4) Date: Nov. 12, 2008

(87) PCT Pub. No.: WO2008/064389
PCT Pub. Date: Jun. 5, 2008

(65) Prior Publication Data
US 2009/0247948 A1 Oct. 1, 2009

(30) Foreign Application Priority Data
Nov. 28, 2006 (AU) ................................ 2006906657

(51) Int. Cl.
*A61M 5/00* (2006.01)
*A61M 5/32* (2006.01)
(52) U.S. Cl. ................ 604/110; 604/195; 604/196
(58) Field of Classification Search .................. 604/110, 604/195, 196
See application file for complete search history.

(56) References Cited

U.S. PATENT DOCUMENTS

| | | |
|---|---|---|
| 5,931,813 A | 8/1999 | Liu |
| 6,033,385 A | 3/2000 | Liu |
| 6,391,008 B1 * | 5/2002 | Tsai ............................ 604/195 |
| 7,056,301 B2 * | 6/2006 | Liu ............................. 604/110 |
| 2003/0065290 A1 * | 4/2003 | Shyu ........................... 604/187 |
| 2003/0212367 A1 * | 11/2003 | Shue et al. ................... 604/196 |
| 2004/0122364 A1 | 6/2004 | Lee |
| 2005/0113751 A1 * | 5/2005 | Chen ........................... 604/110 |

FOREIGN PATENT DOCUMENTS

| | | |
|---|---|---|
| FR | 2730937 | 8/1996 |
| WO | WO 2004/000039 A1 | 12/2003 |

OTHER PUBLICATIONS

International Search Report dated Jul. 23, 2007 from PCT Patent Application No. PCT/AU2007/000779.

* cited by examiner

*Primary Examiner* — Nicholas Lucchesi
*Assistant Examiner* — Ian Holloway
(74) *Attorney, Agent, or Firm* — Wolf, Greenfield & Sacks, P.C.

(57) ABSTRACT

A retractable syringe (30) comprising a hollow barrel (32) with a radially inwardly facing abutment surface (54) and a needle hub (40) having first engagement formation (42) integrally formed with the needle hub. A radially outer portion (50) of the first engagement formation (42) is engaged with the abutment surface (54) to radially inwardly bias the first engagement formation (42). A plunger includes a second engagement formation (60) which the first engagement formation captively engages at the end of a stroke thereby engaging the plunger (34) with the needle hub (40). The needle tip is retractable into the barrel (34) upon application of a predetermined longitudinal force to the plunger (34).

13 Claims, 21 Drawing Sheets

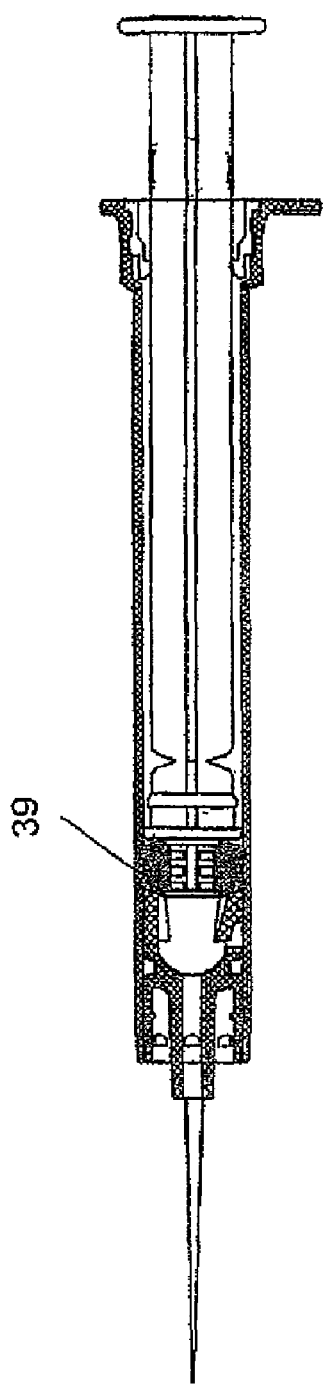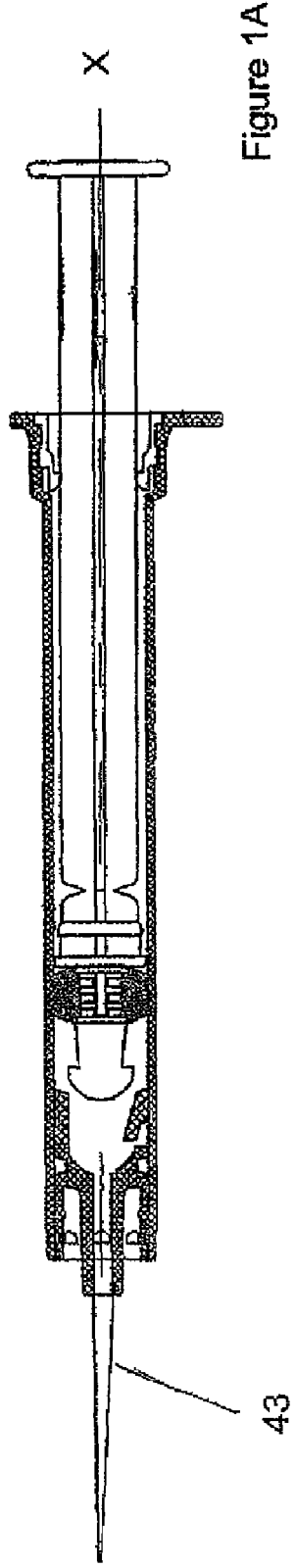
Figure 1B
Figure 1A

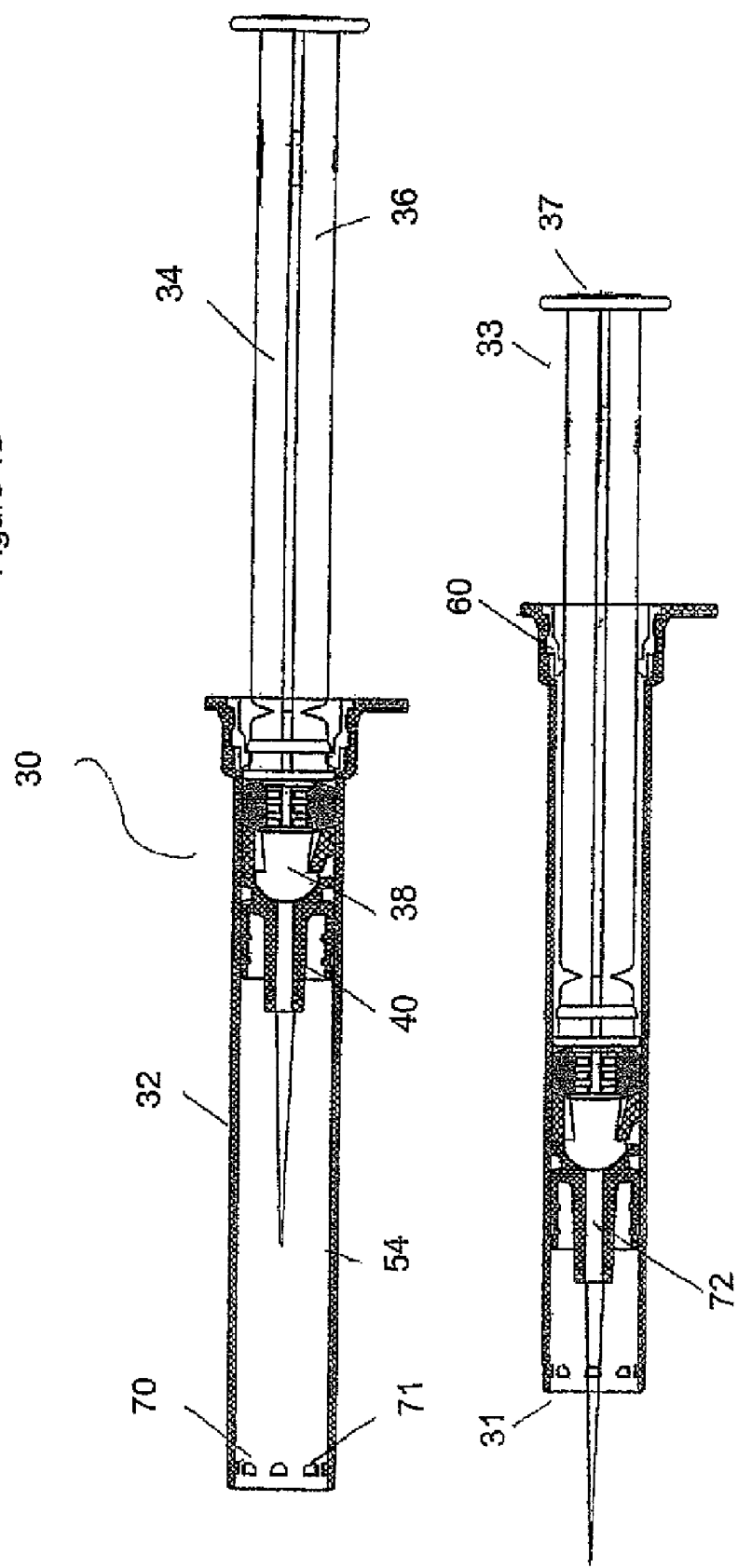

RETRACTABLE SYRINGE

FIELD OF THE INVENTION

The present invention relates to a retractable syringe. In particular, the present invention relates to a retractable syringe suitable for single use delivery of medication and vaccinations.

BACKGROUND OF THE INVENTION

The risk of disease transmission resulting from the incorrect use or disposal of syringes is a serious problem around the world.

Diseases such as HIV (Human Immuno-deficiency Virus) and Hepatitis B along with other blood borne diseases are readily transmitted between persons when a contaminated needle tip comes into contact with and penetrates the skin of a third party.

Protocols exist in hospitals and medical facilities which dictate that a used syringe must be disposed of in a sharps waste unit immediately after an injection has been given. However, the risk still exists of a medical practitioner or other person being injured by the needle tip in a needle stick injury during the disposal of the syringe.

The problem of correct syringe disposal is particularly prevalent amongst intravenous drug users who commonly dispose of syringes without paying head to standard disposal protocols. The discarding of syringes in public places puts the population at risk of needle stick injuries.

The spread of blood borne diseases through the re-use of syringes is a significant problem amongst intravenous drug users. When a needle is refilled after an injection and subsequently injected by another person without adequate sterilisation, there is a serious risk of any diseases carried by the first person being transmitted to the second person.

A retractable syringe has been proposed in which a metallic clip is affixed to the head of the syringe plunger. As the plunger is pushed within the barrel during an injection stroke, the metallic clip frictionally engages with an internal wall of a needle hub, causing the head of the plunger to lock within the needle hub. A subsequent withdrawal of the plunger causes the needle hub, and the needle tip to retract within the body of the barrel, preventing a user or other person from accidentally coming into contact with the needle tip.

However, a problem associated with such retractable syringes is that they are typically more expensive to manufacture than conventional, non-retractable syringes. A further problem is that the metallic clip is known to occasionally not adequately engage with the needle hub. Accordingly, the retractability of the syringe may not operate in all syringes from a given batch. Clearly this is unfavourable in medical applications where syringe malfunction is not acceptable and places the user at risk.

OBJECT OF THE INVENTION

It is the object of the present invention to substantially overcome or at least ameliorate one or more of the above disadvantages, or at least to provide a useful alternative to existing retractable syringes.

SUMMARY OF THE INVENTION

In a first aspect, the present invention provides a retractable syringe comprising:

a hollow barrel having a longitudinal axis extending in a longitudinal direction between a leading end and a trailing end of said barrel;

a radially inwardly facing abutment surface which is fixed in relation to said barrel or forms part of said barrel;

a needle hub mounted at said leading end of said barrel, said needle hub having a needle hub body and a first engagement formation integrally formed with said needle hub body, said first engagement formation having a leading end and a trailing end, said trailing end of said first engagement formation being joined to said needle hub body, wherein a radially outer portion of the first engagement formation is engaged with said abutment surface to radially inwardly bias the leading end of the first engagement formation;

a needle tip connected to and in fluid communication with said needle hub body; and a plunger insertable within said barrel, said plunger having a stem and a head, said head including a second engagement formation;

said plunger being displaceable through a longitudinal stroke in said longitudinal direction to an end of said stroke in which said first engagement formation captively engages said second engagement formation, thereby engaging the plunger with the needle hub, said needle tip being retractable into said barrel, after engagement of said first engagement formation with said second engagement formation, upon application of a predetermined longitudinal force to said plunger in a retraction direction of the longitudinal stroke.

The needle hub body preferably includes a rearwardly facing recess adapted to receive the head, further wherein the first engagement formation is integrally formed with a wall of the recess and the leading end of the first engagement formation is biased into the recess by engagement of the abutment surface with the radially outer portion of the first engagement formation.

The first engagement formation is preferably defined by a cut-out formed in the wall.

The radially outer portion of the first engagement formation preferably includes a radially extending projection engaged with the abutment surface.

The abutment surface is preferably an inner wall of the barrel.

The abutment surface is formed on a gland member located between the needle hub body and the barrel.

The trailing end of the first engagement formation preferably includes a region of reduced cross-sectional area, the region of reduced cross-sectional permitting the leading end of the first engagement formation to be radially displaceable.

The second engagement formation preferably includes a shoulder formed in the head, the shoulder being an annular shoulder formed in a radially outer surface of the head.

The head preferably includes a dome shaped leading portion adapted to radially outwardly guide the leading end of the first engagement formation towards the annular shoulder.

In a second aspect, the present invention provides a method of assembling the syringe described above, said method including the steps of:

inserting said needle hub into the barrel and pushing the needle hub in the longitudinal direction to a position near the leading end of the barrel, such that the radially outer portion of the first engagement formation engages with said abutment surface to radially inwardly bias the leading end of the first engagement formation; and inserting the head of the plunger into the trailing end of the barrel.

The step of engaging the radially outer portion of the first engagement formation with the abutment surface preferably includes inwardly biasing the leading end of the first engagement formation into a rearwardly facing recess formed in the hub body.

The method preferably further includes the step, prior to inserting the needle hub into the barrel, of nesting the needle hub within a recess formed in the trailing end of a gland member.

The method preferably includes the step of securing the gland member to the leading end of the barrel.

BRIEF DESCRIPTION OF THE DRAWINGS

Preferred embodiments of the present invention will now be described, by way of example only, with reference to the accompanying drawings in which:

FIGS. 1A to 1D are cross-sectional views of a retractable syringe according to a first embodiment, showing different piston locations along the injection and retraction strokes;

DETAILED DESCRIPTION OF THE PREFERRED EMBODIMENTS

Figure 2:
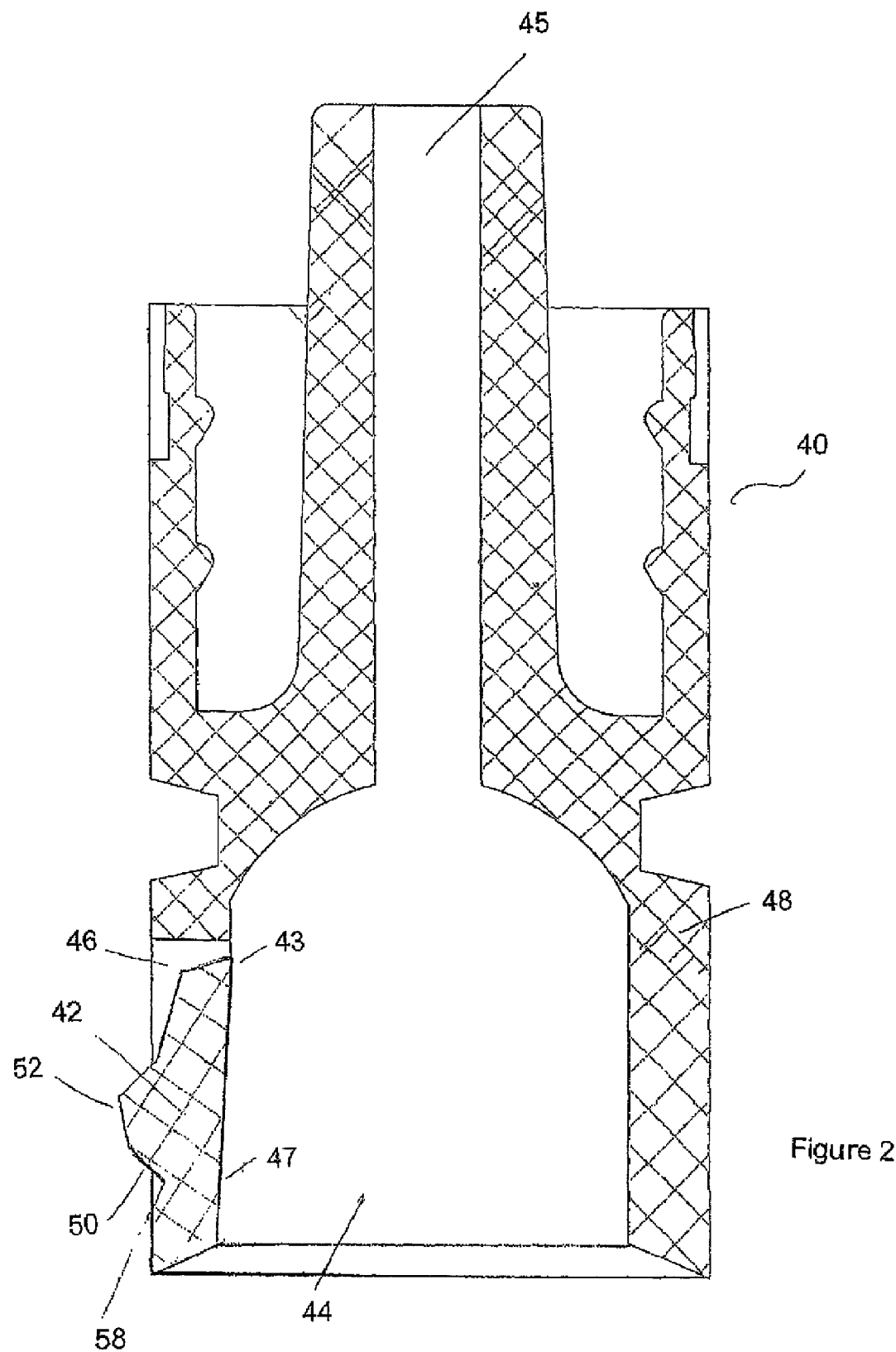
FIG. 2 is a cross-sectional view of a needle hub according to the first embodiment.

A first embodiment of a syringe is shown in FIGS. 1 to 8. The syringe 30 includes a hollow barrel 32 having a longitudinal axis X extending in a longitudinal direction between a leading end 31 and a trailing end 33 of the barrel 32. The syringe 30 includes a plunger 34 which is insertible within the barrel 32 through an opening in the trailing end 33 of the syringe 30. The plunger 34 has a stem 36 which is connected to a head 38. The plunger also includes a rubber piston 39 which is shown in cross section in FIG. 8. The trailing end of the stem 36 has a push plate 37 which is pushed by a user's thumb during an injection.

The syringe 30 includes a needle hub 40 having a needle hub body and a first engagement formation 42. The needle hub 40 is initially located towards the leading end 31 of the barrel 32 prior to use of the syringe 30 as shown in FIG. 1a.

The needle hub 40 is manufactured by injection moulding from a plastic material such as medical grade polypropylene. As shown in FIG. 2, the needle hub 40 includes a recess 44 which is adapted to receive the head 38. The recess 44 has a generally cup shaped profile. The rounded end of the recess 44 located toward the leading end 31 of the barrel 32 is in fluid communication with a needle tip receiving channel 45. A needle tip 43 is interferingly and permanently fitted within the channel 45.

The first engagement formation 42 as seen in FIG. 2 is integrally formed in the needle hub 40 and is in the form of a longitudinally extending finger. The first engagement formation 42 has a leading end 43 and a cantilevered trailing end 47 and is integrally formed within a side wall of the recess 44 toward the trailing end 33 of the needle hub 40. The first engagement formation 42 is defined by a cut-out 46 formed in the wall 48 of the needle hub 40. The cut-out 46 has a generally inverted U shaped profile.

There may be one or more additional first engagement formations 42 spaced around the circumference of the needle hub 40.

A radially outer portion 50 of the first engagement formation 42 is engageable with a radially inwardly facing abutment surface 54 of the syringe 30 to radially inwardly displace the leading end 43 of the first engagement formation 42. The radially outer face 50 includes a radially extending projection 52. As seen in FIG. 2, the projection 52 projects radially beyond the side wall 48 of the needle hub 40 prior to mounting of the needle hub 40 within the barrel 32. In the first embodiment, the abutment surface 54 of the syringe 30 which engages with the projection 52 is an inner cylindrical wall 54 of the barrel.

When viewed in cross-section, the leading end 43 of the first engagement formation 42 has a generally tapered profile which begins at the leading end 43 with a small cross sectional area, and tapers to a greater cross section towards the projection 52.

The trailing end 47 of the first engagement formation 42 includes a region of 20 reduced cross-sectional area 58 in the form of a V shaped notch 58 formed in a radially outer surface of the wall 48. The notch 58 is located between the base of the needle hub 40 and the projection 52, in the vicinity of the cantilevered trailing end 47.

The region of reduced cross-sectional area 58 assists the leading end 43 of the first engagement formation 42 to be displaced radially inwardly in an elastically deformable fashion.

Figure 5:
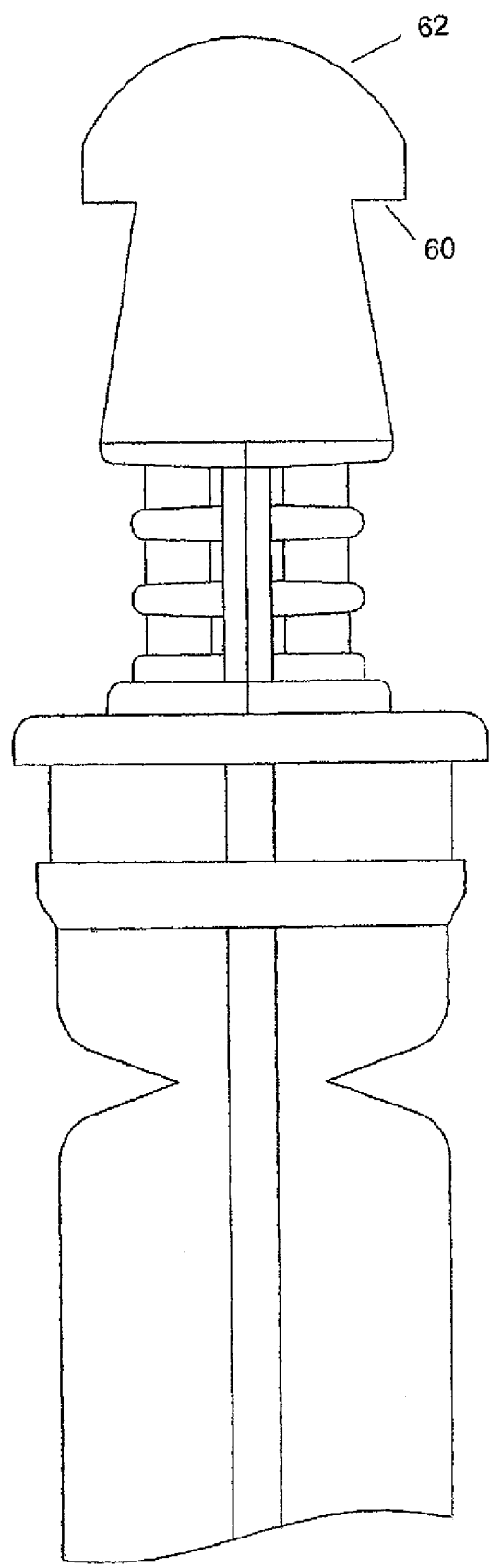
FIG. 5 shows a leading end of the plunger of the first embodiment.
Figure 6:
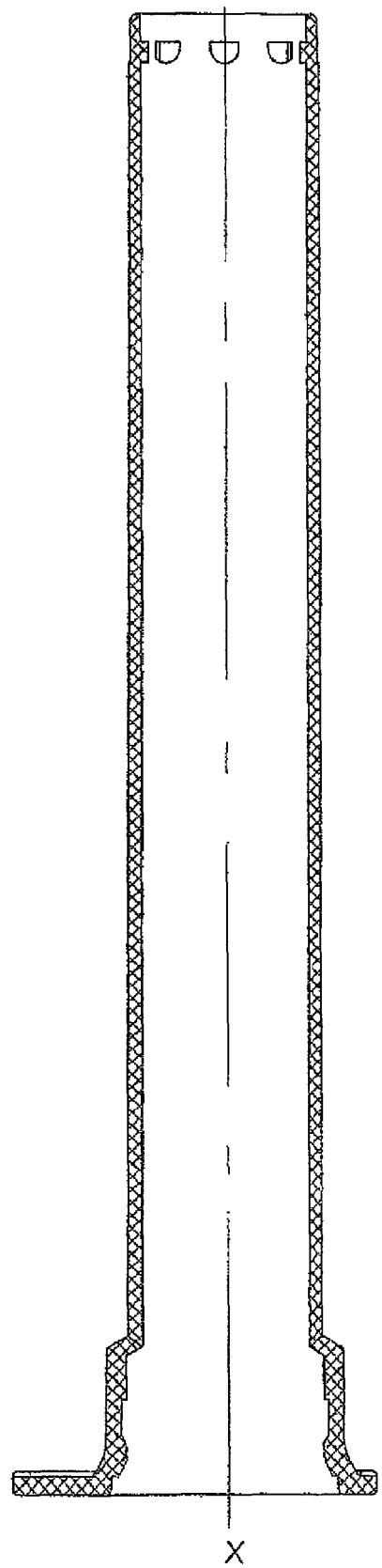
FIG. 6 shows a barrel according to the first embodiment.
Figure 7:
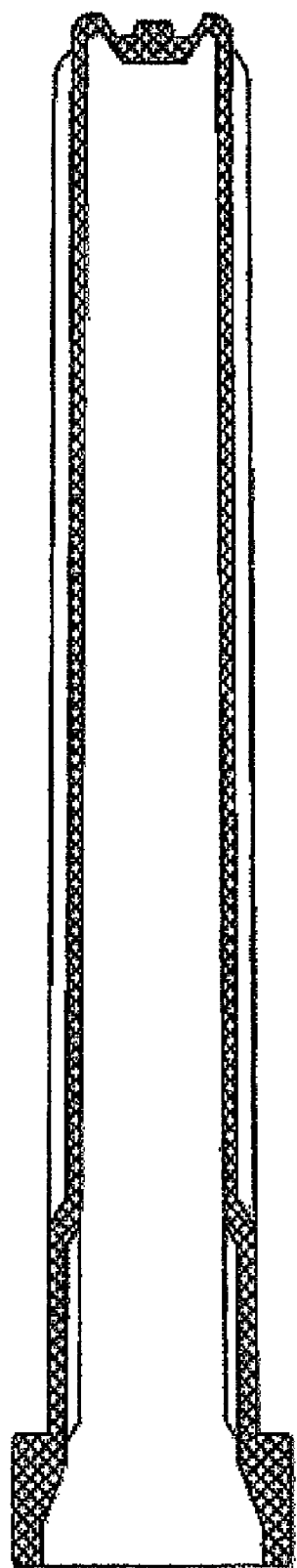
FIG. 7 is a sectional side view of a needle cap.
Figure 8:
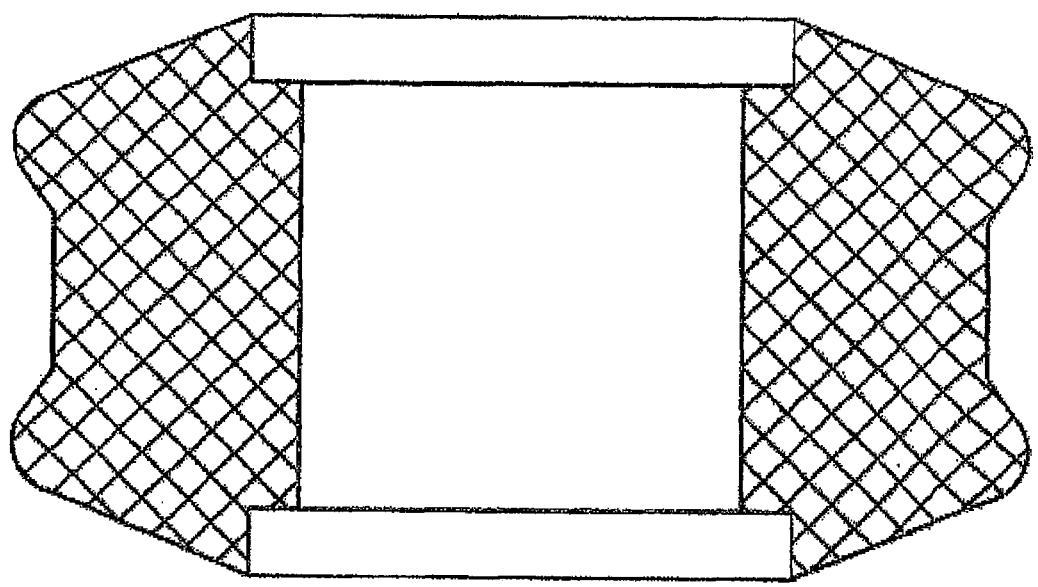
FIG. 8 is a sectional view of a piston of a syringe.
Figure 9:
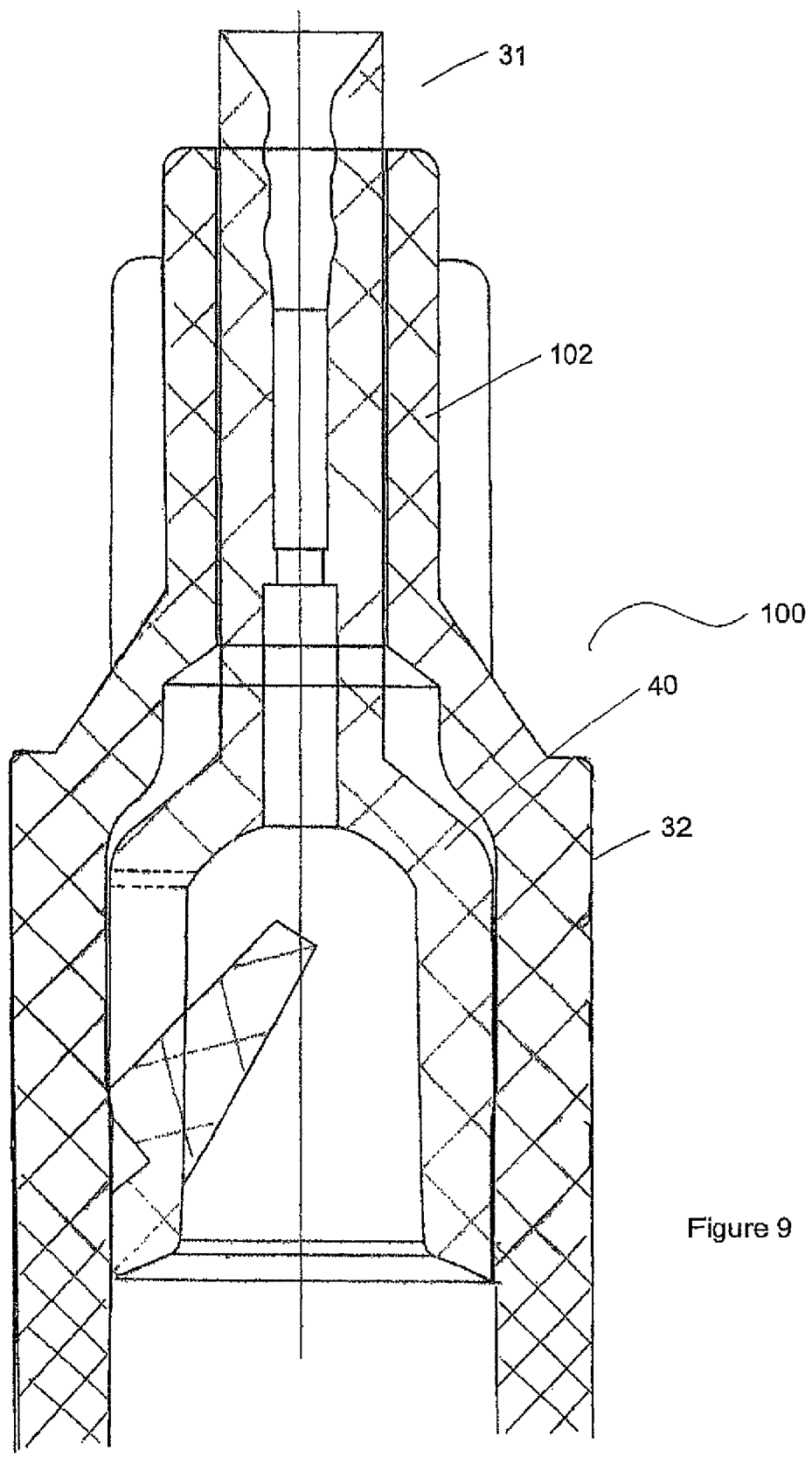
FIG. 9 shows a needle hub and a leading portion of the needle barrel according to a second embodiment.
Figure 10:
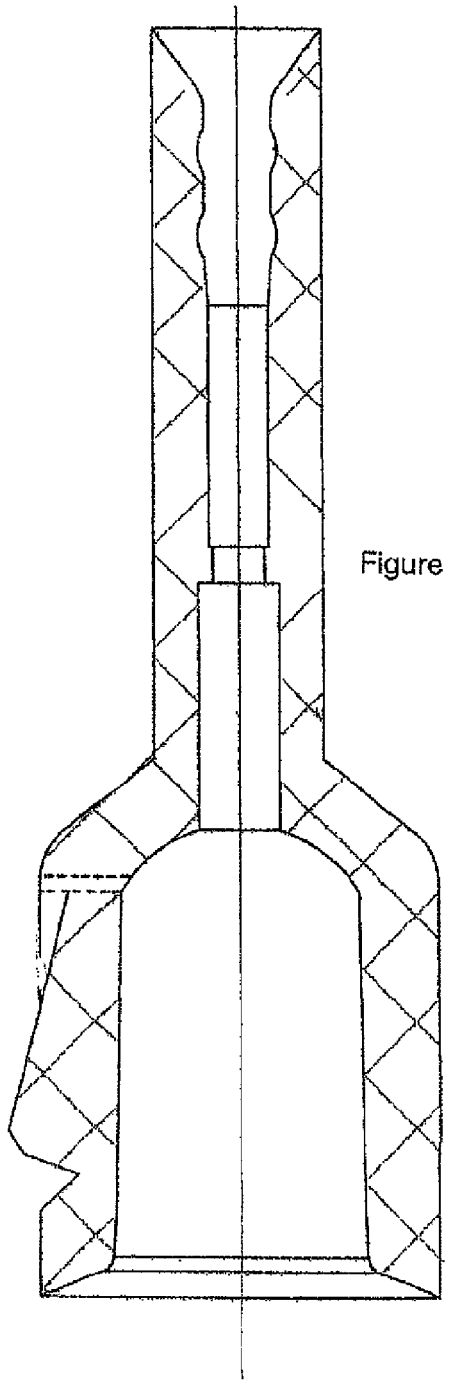
FIG. 10 is a sectional front view of the needle hub of FIG. 9.
Figure 11:
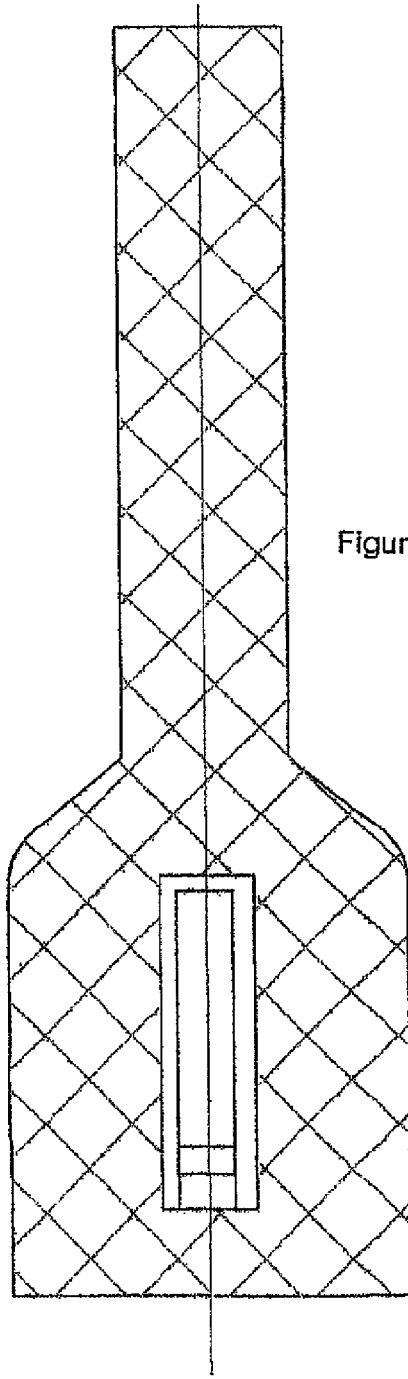
FIG. 11 is a side sectional side view of the needle hub of FIG. 9.
Figure 12:
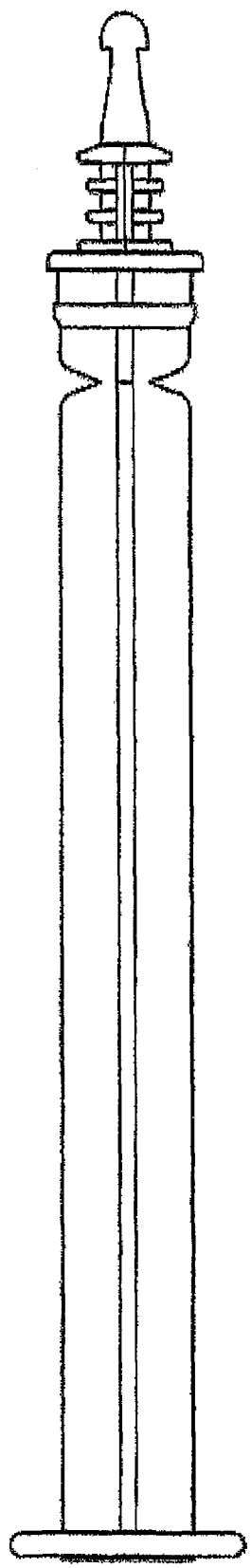
FIG. 12 is a side view of a plunger of the second embodiment.
Figure 13:
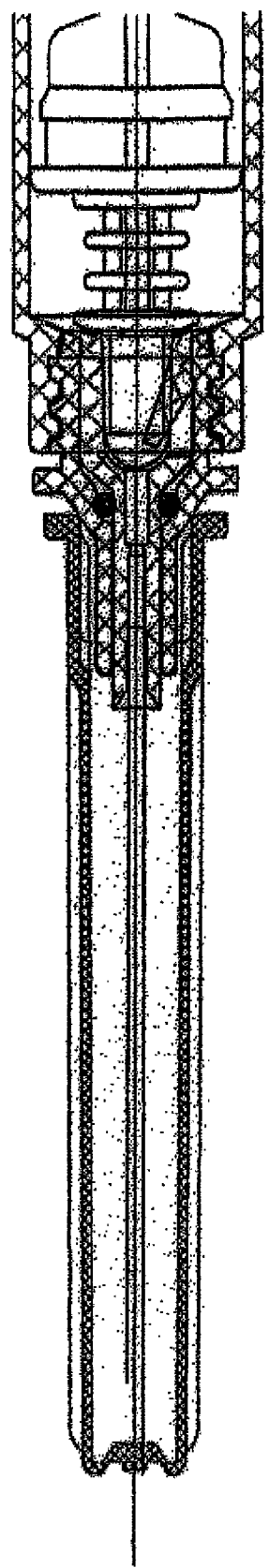
FIG. 13 is a sectional view of the leading end of a syringe according to a third embodiment.
Figure 14:
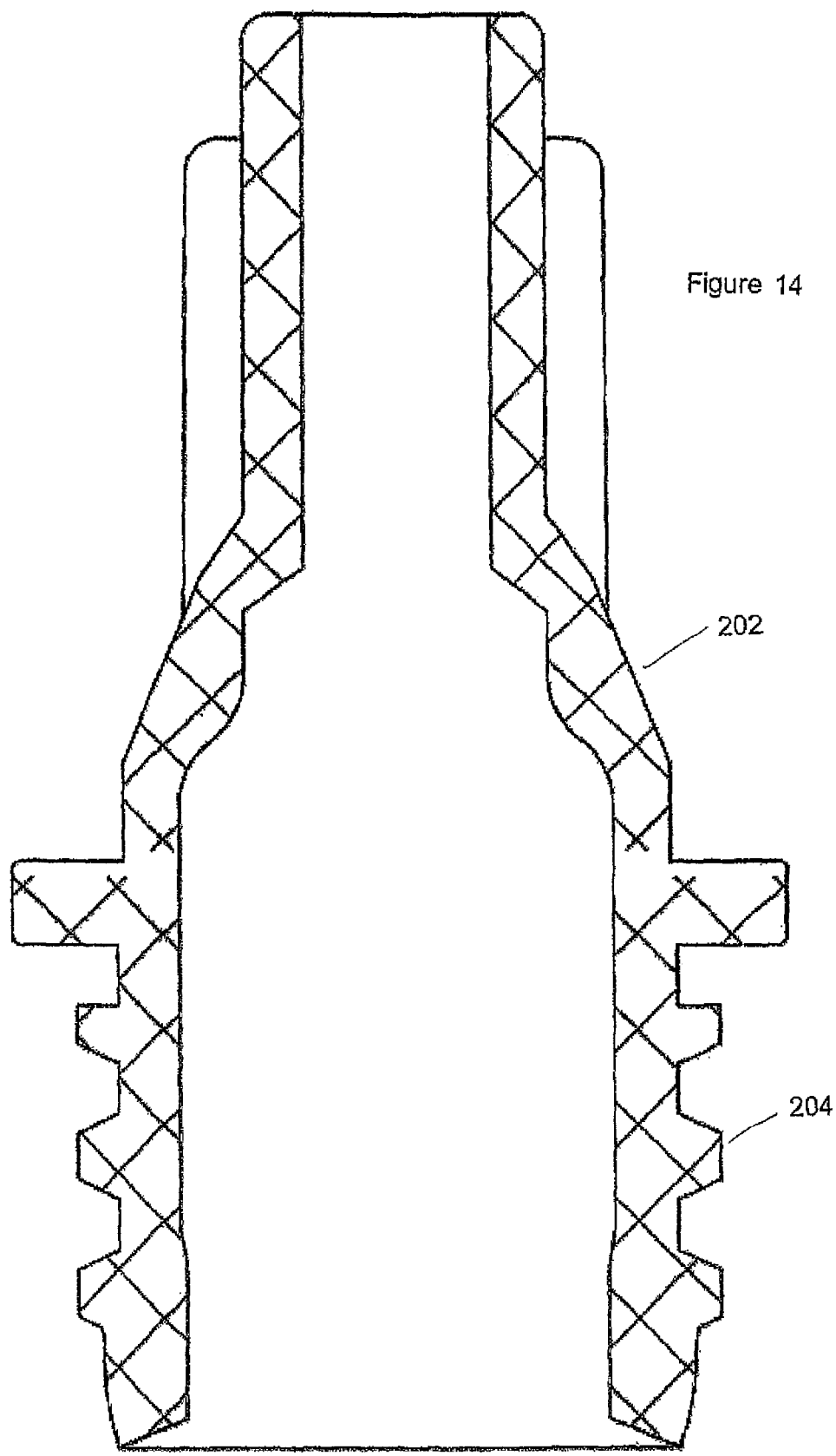
FIG. 14 is a sectional view of a syringe gland according to the third embodiment.
Figure 15:
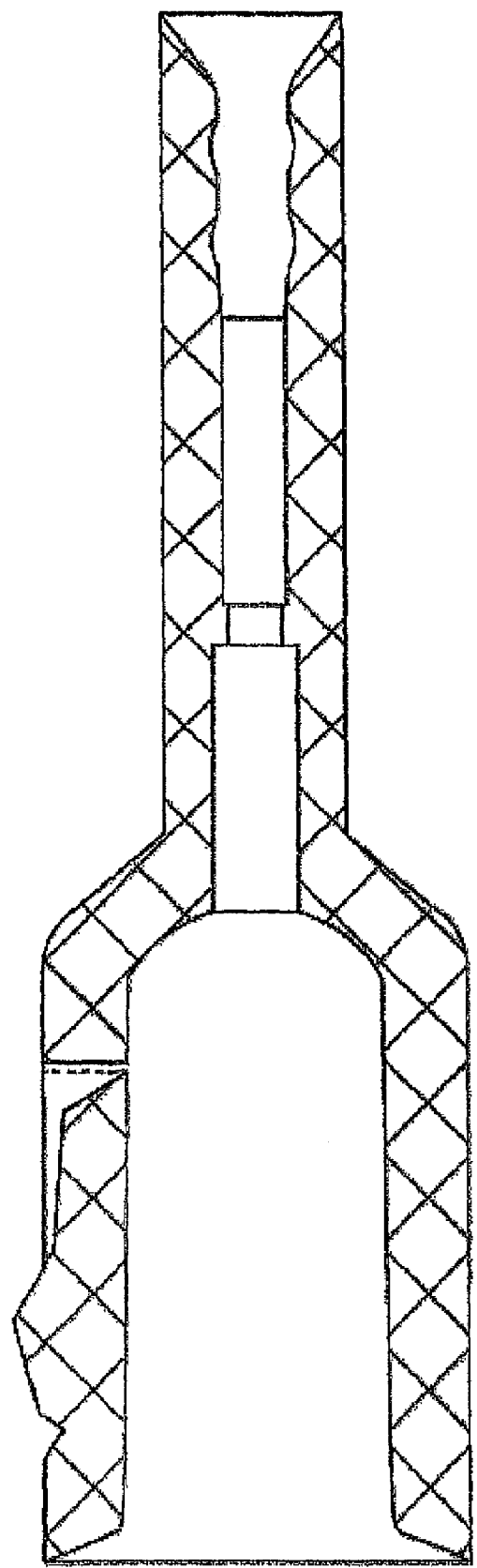
FIG. 15 is a sectional view of a needle hub according to the third embodiment.
Figure 16:
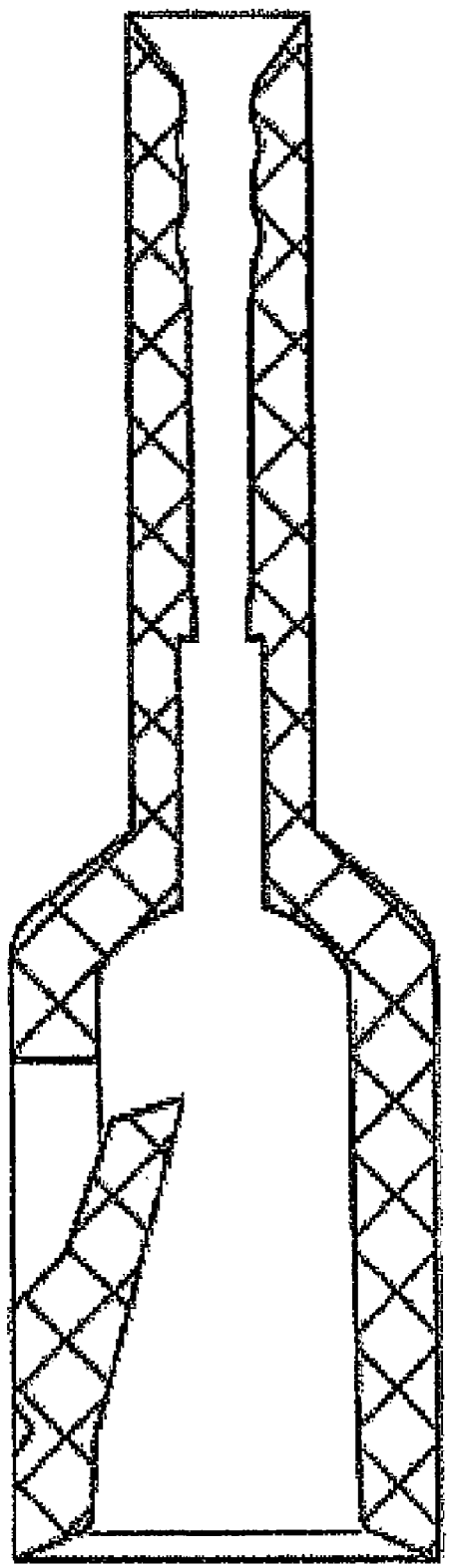
FIG. 16 is a sectional view of the needle hub of FIG. 15 shown in a second mode of operation.

A second engagement formation 60 is formed in the head 38. The second engagement formation 60 is in the form of a shoulder 60 and is best seen in FIG. 5. The shoulder 60 is formed annularly around a radially outer surface of the head 38. The head 38 includes a dome shaped leading portion 62 which radially outwardly guides the leading end of the first engagement formation 42 toward the shoulder 60 during insertion of the plunger 34 within the recess 44. The portion of the head 38 which is on the trailing side of the shoulder 60 has a truncated cone shaped profile which tapers radially outwardly towards the stem 36.

The needle hub 40 is manufactured in a plastic injection moulding operation. The cut-out 46 around the first engagement formation 42 is moulded during manufacture of the needle hub 40. Accordingly, the entire needle hub is made in a single manufacture process. Because the first engagement formation 42 is initially located within the side wall 48 of the recess 44, it does not project within the recess 44 and accordingly does not inhibit removal of a mould core from within the recess 44 during manufacture.

When the abutment surface 54 engages the first engagement formation 42 during assembly, the leading end of the 43 of the first engagement formation 42 projects into the recess 44.

The manufacturing process is simple and less costly than a previously proposed retractable syringe which requires an additional component in the form of a stainless steel clip.

The operation of the first embodiment of the syringe 30 will now be described. During assembly of the syringe 30, the needle hub 40 is inserted through the trailing end 33 of the barrel 32 and pushed towards the leading end 31 of the barrel 32. A restriction 70 in the form of a number of inwardly projecting nodes 71 are located at the leading end 31 of the barrel 32 and prevent the needle hub 40 from exiting from the barrel 32 leading end 31 of the barrel 32. The needle tip 43 projects from the leading end 31 of the barrel 32.

During an injection, the barrel 32 is filled with the medical liquid by inserting the needle tip 43 in a vial of the liquid. Alternatively, the needle may be supplied preloaded with the liquid, for example in the case of some vaccinations. The needle tip 43 is then intravenously or subcutaneously injected into the patient.

Figure 3:
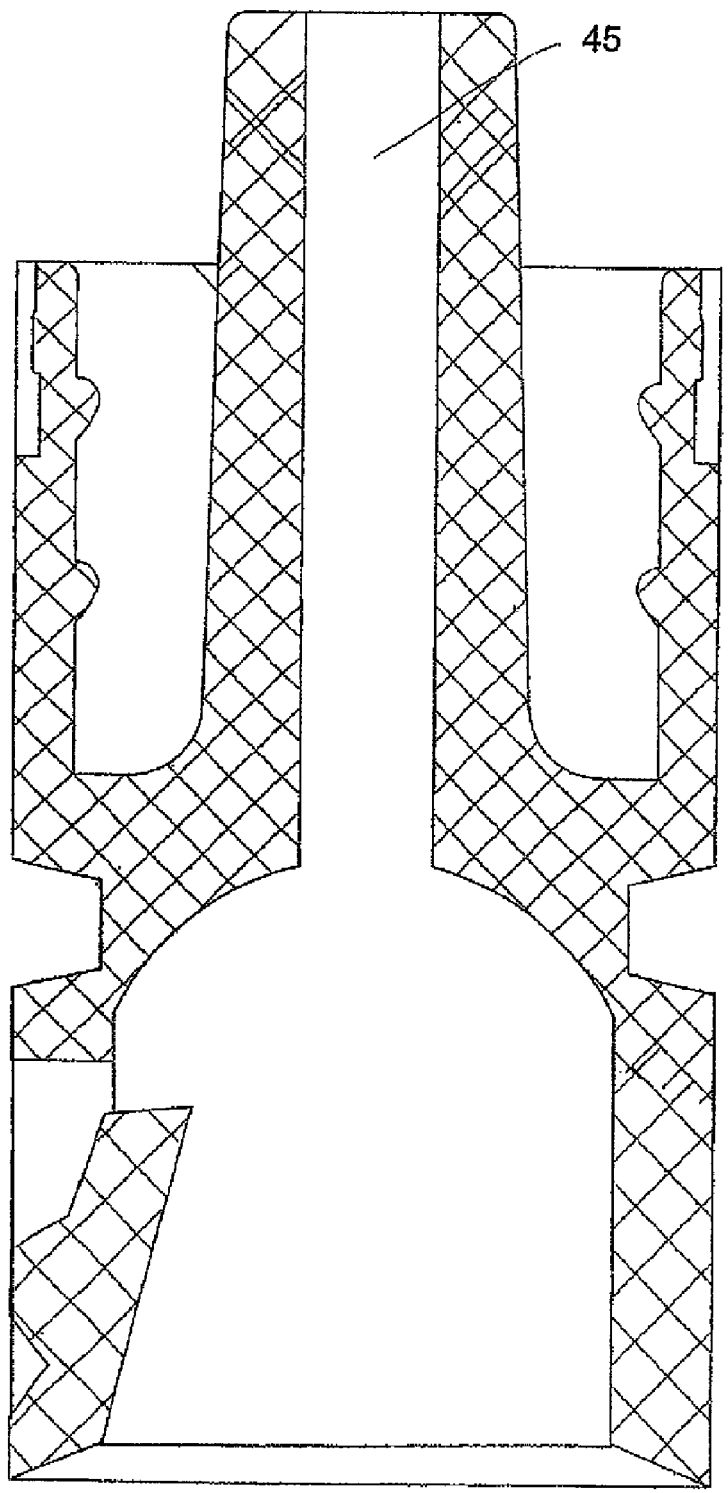
FIG. 3 is a cross-sectional view of the needle hub of FIG. 2, with the longitudinally extending finger shown in a second mode of operation.
Figure 4:
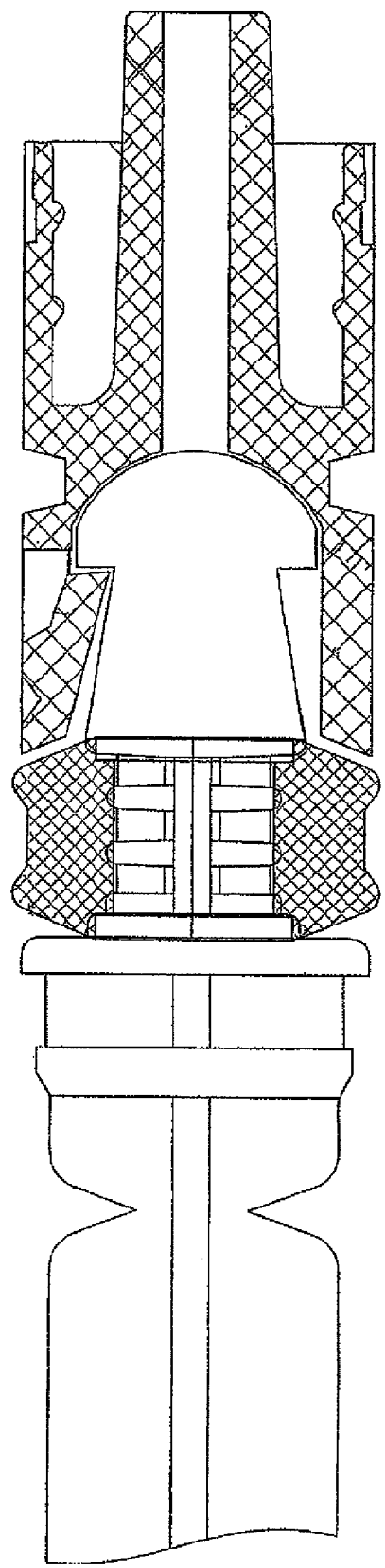
FIG. 4 shows the plunger of the syringe of the first embodiment engaged with the needle hub of FIGS. 2 and 3.

As shown in FIG. 3, the leading end 43 of the first engagement formation 42 initially projects within the recess 44 because the abutment surface 54 of the barrel 32 is in engagement with the protrusion 52.

Application of a force on the push plate 37 with a users thumb causes the plunger 34 to depress into the barrel 32 towards the leading end 31 of the syringe 30. A volume of medical liquid contained within the syringe 30 passes through the channel 45 in the needle hub 40. The liquid accordingly enters the needle tip 43 and subsequently passes into the user's body.

Near an end position of the injection stroke, the head 38 enters the recess 44 and the dome shaped region 62 on the leading end of the head 38 radially outwardly guides the leading end 43 of the first engagement formation 42. When the leading end 43 of the first engagement formation 42 passes the shoulder 60, the first engagement formation 42 springs inwardly to the locked position shown in FIG. 4. In this position, the head 38 is trapped within the recess 44, and the head 38 is captively engaged with the needle hub 40.

Any subsequent attempt which is made to withdraw the plunger from the barrel 32 will result in the head 38 and needle hub 40 being retracted within the barrel 32. Accordingly, the needle tip 43 is also retracted within the syringe 30 to a position where the needle tip 43 is completely shielded inside the barrel 32 and no longer able to come into contact with a person's body. Accordingly the risk of a needle stick injury is significantly reduced at the completion of the retraction process. A locking means 60 may be located at the trailing end 33 of the body of the syringe 30 so that the plunger 34 may be locked to the barrel 32 in the retracted position, so that the needle tip 43 may be permanently prevented from being pushed to the leading end 31 or beyond the leading end 31 of the barrel 32.

A second embodiment of the syringe 100 is shown in FIGS. 9 to 12. The components of the second embodiment which are identical to the first embodiment will not be described. The barrel 32 of the syringe 100 is injection moulded with a restriction 102 at the leading end 31 which acts as a stopper to prevent the needle hub 40 from exiting from the leading end 31, in a similar manner to the restriction 70 of the first embodiment.

A third embodiment of the syringe 200 is shown in FIGS. 13 to 21. The components of the third embodiment which are identical to the first embodiment will not is be described. The syringe 200 includes a gland 202 shown in isolation in FIG. 14. The gland has an external male thread 204 which is engageable with a corresponding female thread 204 formed in the barrel and seen in FIG. 20. The gland 202 is located between the needle hub 40 and the barrel 32.

Similar to the first and second embodiments, a radially outer surface of the first 20 engagement formation 42 is engageable with a radially inwardly facing abutment surface of the syringe 200 to radially inwardly displace the leading end 43 of the first engagement formation 42. The internal surface is in the form of the gland 202.

During assembly of the syringe 200, prior to inserting the needle hub 40 into the barrel 32, the needle hub 40 may be nested within a recess formed in the trailing end of the gland member 202. The gland is then screwed or otherwise fastened to the leading end of the barrel 32.

Figure 17:
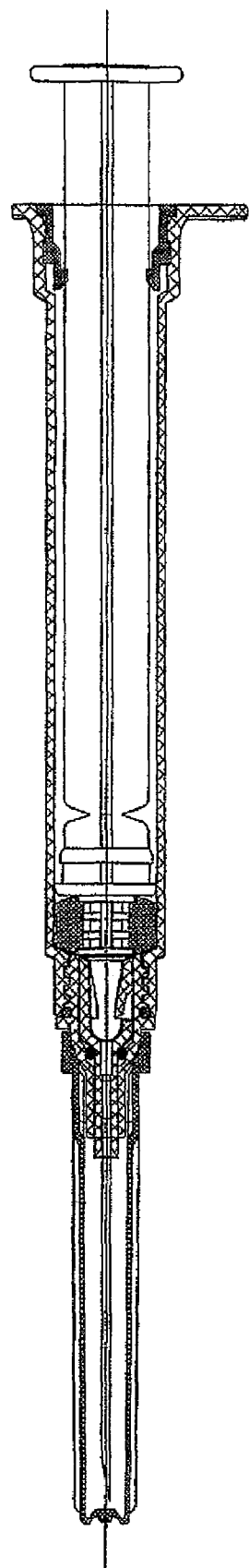
FIG. 17 is a sectional view of a syringe according to the third embodiment, at the end of an insertion stroke.
Figure 18:
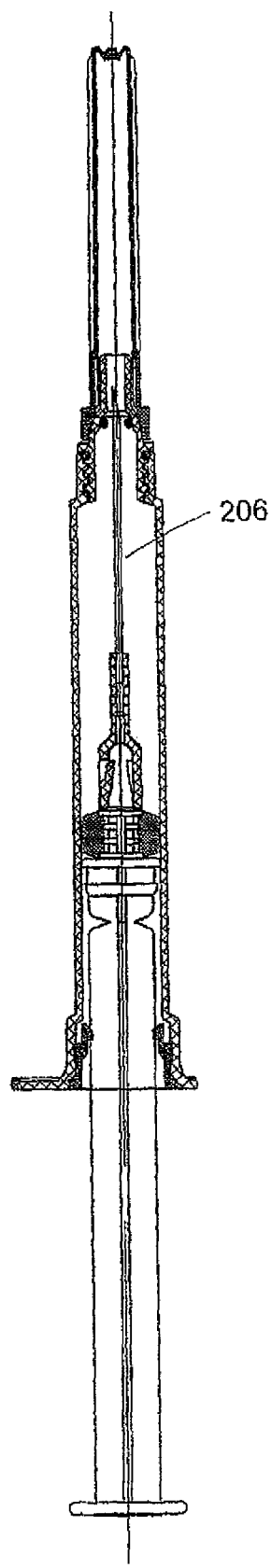
FIG. 18 is a sectional view of the syringe of FIG. 17 after completion of an insertion and retraction stroke.
Figure 19:
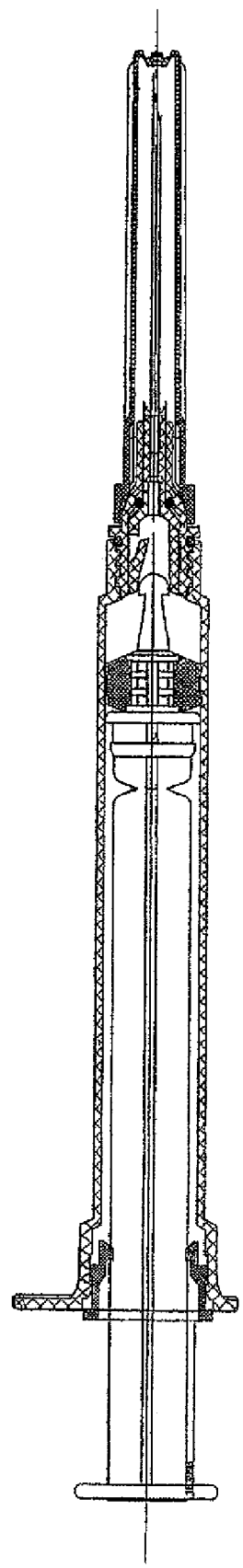
FIG. 19 is a cross-sectional view of the syringe of the third embodiment during insertion of the plunger.
Figure 20:
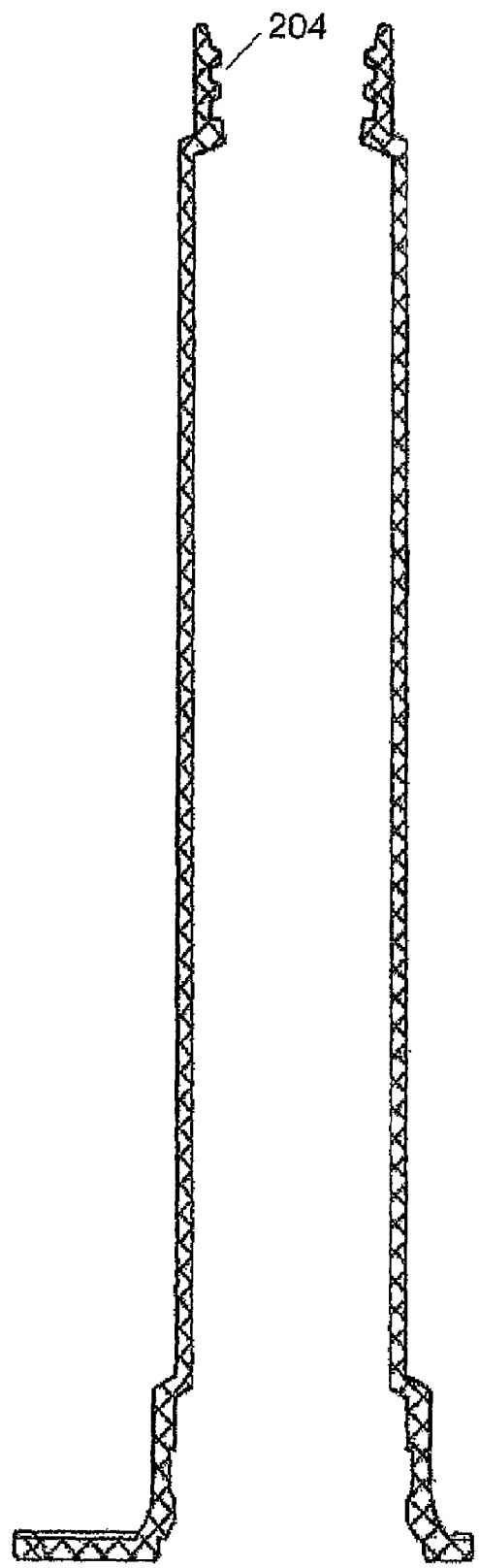
FIG. 20 is a sectional side view of the barrel of the third embodiment.
Figure 21:
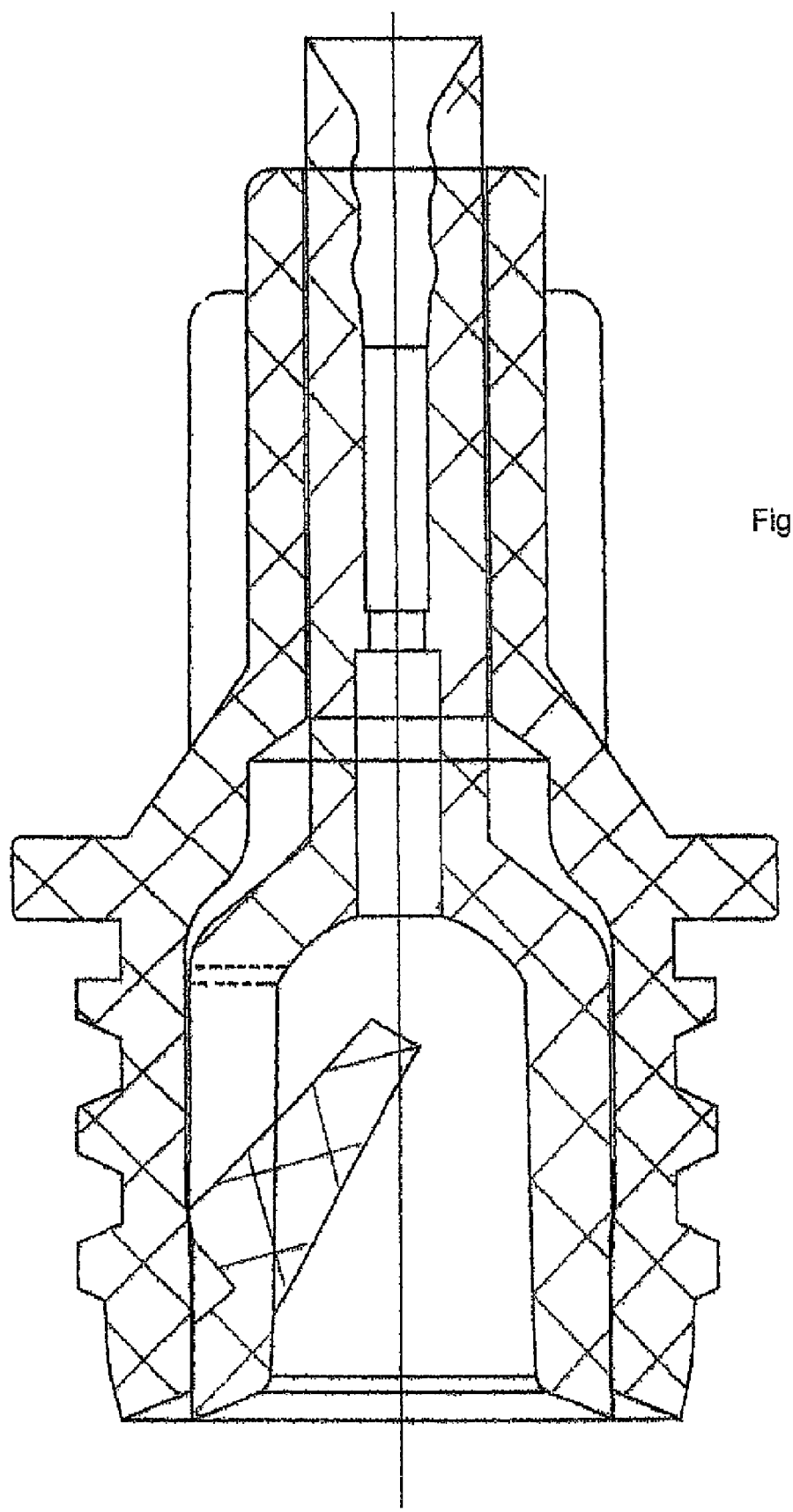
FIG. 21 is a perspective view of the needle hub and gland of the third embodiment.

FIG. 17 shows the syringe 200 of the third embodiment at an end of an injection when the head 38 is captively engaged within the recess 44 of the needle hub 40. FIG. 18 shows a position along the subsequent retraction stroke, at a point where the needle tip 43 is completely shrouded within the barrel 32.

Although the invention has been described with reference to particular examples, it will be appreciated by those skilled in the art that the invention may be embodied in many other forms.

The invention claimed is:

1. A retractable syringe comprising:
   a hollow barrel having a longitudinal axis extending in a longitudinal direction between a leading end and a trailing end of said barrel;
   a radially inwardly facing abutment surface which is fixed in relation to said barrel or forms part of said barrel;
   a needle hub mounted at said leading end of said barrel, said needle hub having a needle hub body and a first engagement formation integrally formed with said needle hub body, said first engagement formation having a leading end and a trailing end, said trailing end of said first engagement formation being joined to said needle hub body, wherein a radially outer portion of the first engagement formation projects radially beyond an exterior side wall of the needle hub prior to mounting of the needle hub within the barrel, and is engaged with said abutment surface after mounting of the needle hub within the barrel to radially inwardly bias the leading end of the first engagement formation;
   a needle tip connected to and in fluid communication with said needle hub body; and
   a plunger insertable within said barrel, said plunger having a stem and a head, said head including a second engagement formation;
   said plunger being displaceable through a longitudinal stroke in said longitudinal direction to an end of said stroke in which the inwardly biased leading end of said first engagement formation captively engages said second engagement formation, thereby engaging the plunger with the needle hub, said needle tip being retractable into said barrel, after engagement of said first engagement formation with said second engagement formation, upon application of a predetermined longitudinal force to said plunger in a retraction direction of the longitudinal stroke.

2. The syringe of claim 1, wherein the needle hub body includes a rearwardly facing recess adapted to receive the head, further wherein the first engagement formation is integrally formed with a wall of said recess and the leading end of the first engagement formation is biased into said recess by engagement of said abutment surface with said radially outer portion of the first engagement formation.

3. The syringe of claim 2, wherein the first engagement formation is defined by a cut-out formed in the wall.

4. The syringe of any one of the preceding claims, wherein the radially outer portion of the first engagement formation includes a radially extending projection engaged with said abutment surface.

5. The syringe of claim 4, wherein said abutment surface is an inner wall of said barrel.

6. The syringe of claim 4, wherein said abutment surface is formed on a gland member located between the needle hub body and the barrel.

7. The syringe of claim 1, wherein the trailing end of the first engagement formation includes a region of reduced cross-sectional area, the region of reduced cross-sectional permitting the leading end of the first engagement formation to be radially displaceable.

8. The syringe of claim 1, wherein the second engagement formation includes a shoulder formed in the head, the shoulder being an annular shoulder formed in a radially outer surface of is the head.

9. The syringe of claim 8, wherein the head includes a dome shaped leading portion adapted to radially outwardly guide the leading end of the first engagement formation towards the annular shoulder.

10. A method of assembling the syringe of claim 1, said method including the steps of:

inserting said needle hub into the barrel and pushing the needle hub in the longitudinal direction to a position near the leading end of the barrel, such that the radially outer portion of the first engagement formation engages with said abutment surface to radially inwardly bias the leading end of the first engagement formation; and inserting the head of the plunger into the trailing end of the barrel.

11. The method of claim 10, wherein the step of engaging the radially outer portion of the first engagement formation with the abutment surface includes inwardly biasing the leading end of the first engagement formation into a rearwardly facing recess formed in the hub body.

12. The method of claim 10 or 11, further including the step, prior to inserting the needle hub into the barrel, of nesting the needle hub within a recess formed in the trailing end of a gland member.

13. The method of claim 12 including the step of securing the gland member to the leading end of the barrel.

* * * * *